United States Patent [19]
Schuster et al.

[11] Patent Number: 5,869,251
[45] Date of Patent: *Feb. 9, 1999

[54] USE OF PRIMERS CONTAINING NUCLEOTIDES HAVING ALTERED BASE PAIRING CHARACTERISTICS IN THE AMPLIFICATION OF NUCLEIC ACID MOLECULES

[75] Inventors: David M. Schuster, Poolesville; Ayoub Rashtchian, Gaithersburg, both of Md.

[73] Assignee: Life Technologies, Inc., Rockville, Md.

[*] Notice: The term of this patent shall not extend beyond the expiration date of Pat. No. 5,578,467.

[21] Appl. No.: 755,736

[22] Filed: Nov. 25, 1996

Related U.S. Application Data

[63] Continuation of Ser. No. 246,921, May 20, 1994, Pat. No. 5,578,467, which is a continuation of Ser. No. 819,132, Jan. 10, 1992, abandoned.

[51] Int. Cl.[6] .............................. C12Q 1/68; C12P 19/34
[52] U.S. Cl. ........................... 435/6; 435/91.2; 435/91.52
[58] Field of Search .......................... 435/6, 91.2, 91.52; 536/24.33; 935/78

[56] References Cited

U.S. PATENT DOCUMENTS

| | | | |
|---|---|---|---|
| 4,683,194 | 7/1987 | Saiki et al. | 435/6 |
| 4,683,202 | 7/1987 | Mullis | 435/91 |

FOREIGN PATENT DOCUMENTS 329 822  8/1989  European Pat. Off. .

OTHER PUBLICATIONS

Butzer et al., *Genomics* 9, 481–487 (1991).
Meinkoth et al., *Analyt. Biochem.* 138, 267–284 (1984).
Batzer et al., *Nucl. Acids Res.* 19(18), 5081 (1991).
Ehlen et al., *Biochem. Biophys. Res. Comm.* 160(2), 441–447 (1989).
Loh et al., *Science* 243, 217–220 (1989).
Martin et al., *Nucl. Acids Res.* 13(24), 8927–8938 (1985).
Ohtsuka et al., *J. Biol. Chem.* 260(5), 2605–2608 (1985).
Varshney et al., *Nucl. Acids Res.* 16(9), 4162 (1988).
Barany, *Proc. Natl. Acad. Sci USA* 88, 189–193 (1991).
Knoth, K. et al., *Nucleic Acids Research* 16:10932 (1988).
Frohman, M.A. et al., *Proc. Natl. Acad. Sci. (U.S.A.)* 85:8998–9002 (1988).
Frohman, M.A., *PCR Protocols, A Guide to Methods and Applications* pp. 28–38 (Academic Press, NY, 1990).
Loh, E.Y., et al., *Science* 243:217 (1989).
Ohara, O. et al., *Proc. Natl. Acad. Sci. (U.S.A.)* 86:5673 (1989).
Fordham–Skelton, A.P. et al., *Molec. Gen. Genet.* 221:134–138 (1990).
Patil, R.V., *Nucl. Acids Res.* 18:3080 (1990).
Barker, R., *Organic Chemistry of Biological Molecules* Prentice Hall, NJ (1971), pp. 331–336.
Mullis, K. et al., *Cold Spring Harbor Symp. Quant. Biol.* 51:263–273 (1986).
Saiki, R.K. et al., *Bio/Technology* 3:1008–1012 (1985).
Shymala, V. et al., *Gene* 84:1–8 (1989).
Tannich, E. et al., *Anal. Biochem.* 188:255–258 (1989).

*Primary Examiner*—Kenneth R. Horlick
*Attorney, Agent, or Firm*—Howrey & Simon; Jeffrey I. Auerbach; Kevin W. McCabe

[57] ABSTRACT

The present invention provides improved methods for amplifying a nucleic acid molecule. More specifically, the invention involves replacing at least one nucleotide of an oligonucleotide with a nucleotide having altered base pairing characteristics, so as to more equalize the efficiency with which that oligonucleotide and a second oligonucleotide hybridize to a target molecule and then amplifying the target molecule using, for example, the polymerase chain reaction. Improved amplification results from the improvement in relative hybridization efficiencies.

17 Claims, 4 Drawing Sheets

USE OF PRIMERS CONTAINING NUCLEOTIDES HAVING ALTERED BASE PAIRING CHARACTERISTICS IN THE AMPLIFICATION OF NUCLEIC ACID MOLECULES

This application is a continuation of application Ser. No. 08/246,921, filed May 20, 1994, U.S. Pat. No. 5,578,467, which is a continuation of application Ser. No. 07/819,132, filed Jan. 10, 1992, abandoned.

FIELD OF THE INVENTION

The present invention is in the field of recombinant DNA technology. This invention is directed to a process for amplifying a nucleic acid molecule, and to the molecules employed and produced through this process.

BACKGROUND OF THE INVENTION

Assays capable of detecting the presence of a particular nucleic acid molecule in a sample are of substantial importance in forensics, medicine, epidemiology and public health, and in the prediction and diagnosis of disease. Such assays can be used, for example, to identify the causal agent of an infectious disease, to predict the likelihood that an individual will suffer from a genetic disease, to determine the purity of drinking water or milk, or to identify tissue samples. The desire to increase the utility and applicability of such assays is often frustrated by assay sensitivity. Hence, it would be highly desirable to develop more sensitive detection assays.

Nucleic acid detection assays can be predicated on any characteristic of the nucleic acid molecule, such as its size, sequence, and, if DNA, susceptibility to digestion by restriction endonucleases, etc. The sensitivity of such assays may be increased by altering the manner in which detection is reported or signaled to the observer. Thus, for example, assay sensitivity can be increased through the use of detectably labeled reagents. A wide variety of such labels have been used for this purpose. Kourilsky et al. (U.S. Pat. No. 4,581,333) describe the use of enzyme labels to increase sensitivity in a detection assay. Radioisotopic labels are disclosed by Falkow et al. (U.S. Pat. No. 4,358,535), and by Berninger (U.S. Pat. No. 4,446,237). Fluorescent labels (Albarella et al., EP 144914), chemical labels (Sheldon III et al., U.S. Pat. No. 4,582,789; Albarella et al., U.S. Pat. No. 4,563,417), modified bases (Miyoshi et al., EP 119448), etc. have also been used in an effort to improve the efficiency with which detection can be observed.

Although the use of highly detectable labeled reagents can improve the sensitivity of nucleic acid detection assays, the sensitivity of such assays remains limited by practical problems which are largely related to non-specific reactions which increase the background signal produced in the absence of the nucleic acid the assay is designed to detect. Thus, for some applications, such as for the identification of a pure culture of a bacteria, etc., the concentration of the desired molecule will typically be amenable to detection, whereas, for other potential applications, the anticipated concentration of the desired nucleic acid molecule will be too low to permit its detection by any of the above-described assays.

In response to these impediments, a variety of highly sensitive methods for DNA amplification have been developed.

One method for overcoming the sensitivity limitation of nucleic acid concentration is to selectively amplify the nucleic acid molecule whose detection is desired prior to performing the assay. Recombinant DNA methodologies capable of amplifying purified nucleic acid fragments have long been recognized. Typically, such methodologies involve the introduction of the nucleic acid fragment into a DNA or RNA vector, the clonal amplification of the vector, and the recovery of the amplified nucleic acid fragment. Examples of such methodologies are provided by Cohen et al. (U.S. Pat. No. 4,237,224), Maniatis, T. et al., *Molecular Cloning (A Laboratory Manual)*, Cold Spring Harbor Laboratory, 1982, etc.

Other known nucleic acid amplification procedures include transcription-based amplification systems (Kwoh, D. et al., *Proc. Natl. Acad. Sci. (U.S.A.)* 86:1173 (1989); Gingeras TR et al., PCT appl. WO 88/10315 (priority: U.S. patent applications Ser. Nos. 064,141 and 202,978)). Schemes based on ligation of two (or more) oligonucleotides in the presence of nucleic acid having the sequence of the resulting "di-oligonucleotide", thereby amplifying the di-oligonucleotide, are also known (Wu, D. Y. et al., *Genomics* 4:560 (1989)).

Miller, H. I. et al., PCT appl. WO 89/06700 (priority: U.S. patent application Ser. No. 146,462, filed 21 Jan. 1988), disclose a nucleic acid sequence amplification scheme based on the hybridization of a promoter/primer sequence to a target single-stranded DNA ("ssDNA") followed by transcription of many RNA copies of the sequence. This scheme was not cyclic; i.e. new templates were not produced from the resultant RNA transcripts.

Davey, C. et al. (European Patent Application Publication no. 329,822) disclose a nucleic acid amplification process involving cyclically synthesizing single-stranded RNA ("ssRNA"), ssDNA, and double-stranded DNA (dsDNA). The ssRNA is a first template for a first primer oligonucleotide, which is elongated by reverse transcriptase (RNA-dependent DNA polymerase). The RNA is then removed from resulting DNA:RNA duplex by the action of ribonuclease H (RNase H, an RNase specific for RNA in a duplex with either DNA or RNA). The resultant ssDNA is a second template for a second primer, which also includes the sequences of an RNA polymerase promoter (exemplified by T7 RNA polymerase) 5'-to its homology to its template. This primer is then extended by DNA polymerase (exemplified by the large "Klenow" fragment of *E. coli* DNA polymerase I), resulting as a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

Methods that include a transcription step, e.g. that of Davey, C. et al. (European Patent Application Publication no. 329,822), can increase product by more than a factor of 2 at each cycle. Indeed, as 100 or more transcripts can be made from a single template, factors of increase of 100 or more are theoretically readily attainable. Furthermore, if all steps are performed under identical conditions, no molecule which has finished a particular step need "wait" before proceeding to the next step. Thus amplifications that are based on transcription and that do not require thermo-cycling are potentially much faster than thermo-cycling amplifications which are based on template-dependent primer extension.

In methods which amplify a nucleic acid molecule by template dependent extension, the nucleic acid molecule is used as a template for extension of a nucleic acid primer in a reaction catalyzed by polymerase. For example, Panet and Khorana (*J. Biol. Chem.* 249:5213–5221 (1974) which reference is incorporated herein by reference) demonstrated the replication of deoxyribopoly-nucleotide templates bound to cellulose. Kleppe et al. (*J. Mol. Biol.* 56:341–361 (1971) which reference is incorporated herein by reference) disclosed the use of double- and single-stranded DNA molecules as templates for the synthesis of complementary DNA.

The most widely used method of nucleic acid amplification, the "polymerase chain reaction" ("PCR"), involves template dependent extension (Mullis, K. et al., *Cold Spring Harbor Symp. Quant. Biol.* 51:263–273 (1986); Erlich H. et al., EP 50,424; EP 84,796; EP 258,017, EP 237,362; Mullis, K., EP 201,184; Mullis K. et al., U.S. Pat. No. 4,683,202; Erlich, H., U.S. Pat. No. 4,582,788; and Saiki, R. et al., U.S. Pat. No. 4,683,194), which references are incorporated herein by reference). PCR achieves the amplification of a specific nucleic acid sequence using two oligonucleotide primers complementary to regions of the sequence to be amplified. Extension products incorporating the primers then become templates for subsequent replication steps.

The polymerase chain reaction provides a method for selectively increasing the concentration of a nucleic acid molecule having a particular sequence even when that molecule has not been previously purified and is present only in a single copy in a particular sample. The method can be used to amplify either single or double stranded DNA. The essence of the method involves the use of two oligonucleotides to serve as primers for the template-dependent, polymerase mediated replication of the desired nucleic acid molecule.

The precise nature of the two oligonucleotide primers of the PCR method is critical to the success of the method. As is well known, a molecule of DNA or RNA possesses directionality, which is conferred through the 5'→3' linkage of the sugar-phosphate backbone of the molecule. Two DNA or RNA molecules may be linked together through the formation of a phosphodiester bond between the terminal 5' phosphate group of one molecule and the terminal 3' hydroxyl group of the second molecule. Polymerase dependent amplification of a nucleic acid molecule proceeds by the addition of a 5' nucleoside triphosphate to the 3' hydroxyl end of a nucleic acid molecule. Thus, the action of a polymerase extends the 3' end of a nucleic acid molecule. These inherent properties are exploited in the selection of the two oligonucleotide primers of the PCR. The oligonucleotide sequences of the two primers of the PCR method are selected such that they contain sequences identical to, or complementary to, sequences which flank the sequence of the particular nucleic acid molecule whose amplification is desired. More specifically, the nucleotide sequence of the "first" primer is selected such that it is capable of hybridizing to an oligonuc-leotide sequence located 3' to the sequence of the desired nucleic acid molecule, whereas the nucleotide sequence of the "second" primer is selected such that it contains a nucleotide sequence identical to one present 5' to the sequence of the desired nucleic acid molecule. Both primers possess the 3' hydroxyl groups which are necessary for enzyme mediated nucleic acid synthesis.

In the polymerase chain reaction, the reaction conditions are cycled between those conducive to hybridization and nucleic acid polymerization, and those which result in the denaturation of duplex molecules. In the first step of the reaction, the nucleic acids of the sample are transiently heated, and then cooled, in order to denature any double stranded molecules which may be present. The "first" and "second" primers are then added to the sample at a concentration which greatly exceeds that of the desired nucleic acid molecule. When the sample is incubated under conditions conducive to hybridization and polymerization, the "first" primer will hybridize to the nucleic acid molecule of the sample at a position 3' to the sequence of the desired molecule to be amplified. If the nucleic acid molecule of the sample was initially double stranded, the "second" primer will hybridize to the complementary strand of the nucleic acid molecule at a position 3' to the sequence of the desired molecule which is the complement of the sequence whose amplification is desired. Upon addition of a polymerase, the 3' ends of the "first" and (if the nucleic acid molecule was double stranded) "second" primers will be extended. The extension of the "first" primer will result in the synthesis of a DNA molecule having the exact sequence of the complement of the desired nucleic acid. Extension of the "second" primer will result in the synthesis of a DNA molecule having the exact sequence of the desired nucleic acid.

The PCR reaction is capable of exponential amplification of specific nucleic acid sequences because the extension product of the "first" primer contains a sequence which is complementary to a sequence of the "second" primer, and thus will serve as a template for the production of an extension product of the "second" primer. Similarly, the extension product of the "second" primer, of necessity, contain a sequence which is complementary to a sequence of the "first" primer, and thus will serve as a template for the production of an extension product of the "first" primer. Thus, by permitting cycles of hybridization, polymerization, and denaturation, a geometric increase in the concentration of the desired nucleic acid molecule can be achieved. Reviews of the polymerase chain reaction are provided by Mullis, K. B. (*Cold Spring Harbor Symn. Quant. Biol.* 51:263–273 (1986)); Saiki, R. K., et al. (*BiolTechnology* 3:1008–1012 (1985)); and Mullis, K. B., et al. (*Met. Enzymol.* 155:335–350 (1987), which references are incorporated herein by reference).

PCR technology is useful in that it can achieve the rapid and extensive amplification of a polynucleotide molecule. However, the method requires the preparation of two different primers which hybridize to two oligonucleotide sequences flanking the target sequence. The concentration of the two primers can be rate limiting for the reaction. Although it is not essential that the concentration of the two primers be identical, a disparity between the concentrations of the two primers can greatly reduce the overall yield of the reaction.

All of the above amplification procedures depend on the principle that an end product of a cycle is functionally identical to a starting material. Thus, by repeating cycles, the nucleic acid is amplified exponentially. Methods that use thermo-cycling, e.g. PCR or Wu, D. Y. et al. (*Genomics* 4:560 (1989)), have a theoretical maximum increase of product of 2-fold per cycle, because in each cycle a single product is made from each template. In practice, the increase is always lower than 2-fold. Further slowing the amplification is the time spent in changing the temperature. Also adding delay is the need to allow enough time in a cycle for all molecules to have finished a step. Molecules that finish a step quickly must "wait" for their slower counterparts to finish before proceeding to the next step in the cycle; to shorten the cycle time would lead to skipping of one cycle by the "slower" molecules, leading to a lower exponent of amplification.

One disadvantage of PCR is that it requires the use of two primers, and thus requires that sequence information be available for two regions of the target molecule. This is often a significant constraint. In some situations, only the amino acid sequence encoded by a target sequence is known. To amplify the target sequence, it is necessary to employ sets of degenerate primers (corresponding to each of the possible sequences capable of encoding the amino acid sequence coded for by the two regions of the target molecule). The use of such degenerate primer sets can cause significant priming errors, and thus an decrease amplification efficiency. One means of decreasing the number of members in the primer sets when conducting PCR amplification is through the use of primers containing deoxyinosine at positions of ambiguity (Patil, R. V., *Nucl. Acids Res.* 18:3080 (1990); Fordham-Skelton, A. P. et al., *Molec. Gen. Genet.* 221:134–138 (1990); both of which references are herein incorporated by reference).

A second significant disadvantage of the PCR reaction is that when two different primers are used, the reaction conditions chosen must be selected such that both primers "prime" with similar efficiency. Since the two primers necessarily have different sequences, this requirement can constrain the choice of primers and require considerable experimentation. Furthermore, if one tries to amplify two different sequences simultaneously using PCR (i.e. using two sets of two primers), the reaction conditions must be optimized for four different primers.

SUMMARY OF THE INVENTION

The present invention provides an improved method for equalizing the hybridization efficiency of the primers used in a PCR reaction. It thus comprises an improvement in PCR amplification. The invention achieves this goal by employing a primer molecule which contains pre-determined nucleotides having altered base pairing characteristics.

In detail, the invention provides a method for amplifying the concentration of a nucleic acid molecule using two primers, comprising the steps:

(a) performing the template-dependent extension of a first primer, the primer being hybridized to a first strand of the molecule, wherein the extension forms a second strand of a nucleic acid molecule complementary to the first strand;

(b) performing the template-dependent extension of the second strand, by extending a second primer, the primer being hybridized to the second strand of the molecule, wherein the extension forms a copy of the first strand of the nucleic acid molecule;

(c) performing the template-dependent extension of the copy of the first strand, to thereby form a copy of the second strand of the nucleic acid molecule;

(d) repeating steps (a), (b), and (c), to thereby achieve the amplification of the nucleic acid molecule;

wherein at least one of the first and second primers contains at least one deoxyinosine residue, and wherein the first and second primers have equivalent efficiency of primer extension.

The invention also provides the embodiments of the above method wherein the nucleic acid molecule is an RNA or a DNA molecule, and wherein such molecule is either single-stranded or double-stranded.

The invention also provides the embodiments of the above methods wherein only one of the primers contains at least one deoxyinosine residue, and wherein both of the primers contain at least one deoxyinosine residue.

The invention also provides the embodiment of the above methods wherein the nucleic acid molecule being amplified is polyadenylated at its 3' end, and wherein one of the primers contains a poly-T sequence, and the other of the primers contains at least one deoxyinosine residue.

The invention also provides the embodiment of the above methods wherein the nucleic acid molecule being amplified, copy thereof or complementary copy thereof has been extended to contain a 3' sequence, and wherein one of the primers is capable of hybridizing to the 3' sequence, the primer containing at least one deoxyinosine residue.

The invention also provides the embodiment of the above methods wherein at least one of the primers is extended using a thermostable DNA polymerase, such as Taq polymerase.

The invention also provides a kit for amplifying a nucleic acid molecule containing:

a first container containing a primer, the primer being capable of hybridizing to the nucleic acid molecule, and containing at least one deoxyadenosine residue; and a second container containing an enzyme capable of adding a C nucleotide to the nucleic acid molecule, the C nucleotide being capable of base pairing with the deoxyinosine residue of the primer.

The invention also provides for the above kit which additionally contains a third container containing a thermostable DNA polymerase, such as Taq polymerase capable of extending the primer of the first container, when the primer is hybridized to a sequence containing the C residue added by the enzyme of the second container.

The invention also provides a kit for amplifying a nucleic acid molecule containing:

a first container containing a first primer, the primer being capable of hybridizing to the nucleic acid molecule, and containing at least one deoxyinosine residue; and a second container containing a second primer; wherein template-dependent extension of the first primer produces a second nucleic acid molecule which is capable of hybridizing to the second primer, and wherein template-dependent extension of the second primer produces a copy of the first nucleic acid molecule.

The invention also provides the above kit which additionally contains a third container containing a thermostable DNA polymerase, such as Taq polymerase, capable of extending either the primer of the first container, or the primer of the second container when the primer is hybridized to a nucleic acid molecule.

BRIEF DESCRIPTION OF THE FIGURES

FIGS. 4A–3 shows the use of inosine in the 5' RACE reaction.

DETAILED DESCRIPTION OF THE INVENTION

Figure 1A:
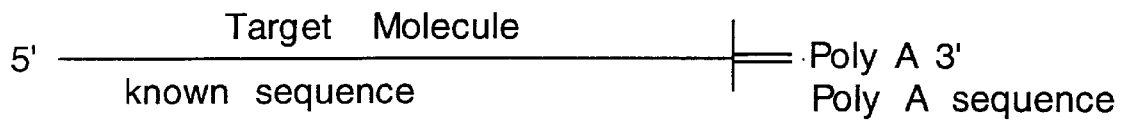
FIGS. 1A–1E shows a depiction of the 3' RACE reaction.

The present invention provides an improved method for amplifying a desired nucleic acid molecule in a sample. Such samples may include biological samples derived from a human or other animal source (such as, for example, blood, stool, sputum, mucus, serum, urine, saliva, teardrop, a biopsy sample, an histology tissue sample, a PAP smear, a mole, a wart, an agricultural product, waste water, drinking water, milk, processed foodstuff, air, etc.) including samples derived from a bacterial or viral preparation, as well as other samples (such as, for example, agricultural products, waste or drinking water, milk or other processed foodstuff, air, etc.).

The method, provided by the present invention, for amplifying a desired nucleic acid molecule in a sample, may be used to amplify any desired nucleic acid molecule. Such molecules may be either DNA or RNA. The molecule may be in either a double-stranded or single-stranded form. However, if the nucleic acid is double-stranded at the start of the amplification reaction it is preferably first treated to render the two strands into a single-stranded, or partially single-stranded, form. Methods are known to render double-stranded nucleic acids into single-stranded, or partially single-stranded, forms, such as heating, or by alkali treatment, or by enzymatic methods (such a by helicase action, etc.), or by binding proteins, etc. General methods for accomplishing this treatment are provided by Maniatis, T., et al. (In: *Molecular Cloning. A Laboratory Manual,* Cold Spring Harbor Laboratories, Cold Spring Harbor, N.Y. (1982)), and by Haymes, B. D., et al. (In: *Nucleic Acid Hybridization. A Practical Approach,* IRL Press, Washington, D.C. (1985)), which references are herein incorporated by reference.

Macromolecular entities that contain nucleic acid other than double-stranded DNA, or single-stranded DNA, such as single-stranded RNA, double-stranded RNA or mRNA are capable of being amplified by the method of the invention. For example, the RNA genomes of certain viruses can be converted to DNA by reaction with enzymes such as reverse transcriptase (Maniatis, T. et al., *Molecular Cloning (A Laboratory Manual*), Cold Spring Harbor Laboratory, 1982; Noonan, K. F. et al., *Nucleic Acids Res.* 16:10366 (1988)). The product of the reverse transcriptase reaction may then be amplified according to the invention.

The nucleic acid molecules which may be amplified in accordance with the present invention may be homologous to other nucleic acid molecules present in the sample (for example, it may be a fragment of a human chromosome isolated from a human cell biopsy, etc.). Alternatively, the molecule may be heterologous to other nucleic acid molecules present in the sample (for example, it may be a viral, bacterial, or fungal nucleic acid molecule isolated from a sample of human blood, stools, etc.). The methods of the invention are capable of simultaneously amplifying both heterologous and homologous molecules. For example, amplification of a human tissue sample infected with a virus may result in amplification of both viral and human sequences.

The present methods do not require that the molecules to be amplified have any particular sequence or length. In particular, the molecules which may be amplified include any naturally occurring procaryotic (for example, pathogenic or non-pathogenic bacteria, Escherichia, Salmonella, Clostridium, Agrobacter, Staphylococcus and Streptomyces, Streptococcus, Rickettsiae, Chlamydia, Nycoplasma, etc.), eukaryotic (for example, protozoans and parasites, fungi, yeast, higher plants, lower and higher animals, including mammals and humans) or viral (for example, Herpes viruses, HIV, influenza virus, Epstein-Barr virus, hepatitis virus, polio virus, etc.) or viroid nucleic acid. The nucleic acid molecule can also be any nucleic acid molecule which has been or can be chemically synthesized. Thus, the nucleic acid sequence may or may not be found in nature.

"Primer" as used herein refers to a single-stranded oligonucleotide or a single-stranded polynucleotide that is extended by covalent addition of nucleotide monomers during amplification. Nucleic acid amplification often is based on nucleic acid synthesis by a nucleic acid polymerase. Many such polymerases require the presence of a primer that can be extended to initiate such nucleic acid synthesis. A primer is typically 11 bases or longer; most prefererably, a primer is 17 bases or longer.

"Reaction" denotes a liquid suitable for conducting a desired reaction (such as amplification, hybridization, cDNA synthesis, etc.).

"Amplification" as used herein refers to an increase in the amount of the desired nucleic acid molecule present in a sample. "Substantial amplification" refers to greater than about three-fold amplification. Any of the primer-extension amplification methods discussed above may be improved in accordance with the present invention.

As used herein, two sequences are said to be able to hybridize or anneal to one another if they are capable of forming an anti-parallel double-stranded nucleic acid structure. Conditions of nucleic acid hybridization suitable for forming such double stranded structures are described by Maniatis, T., et al. (In: *Molecular Cloning. A Laboratory Manual,* Cold Spring Harbor Laboratories, Cold Spring Harbor, N.Y. (1982)), and by Haymes, B. D., et al. (In: *Nucleic Acid Hybridization, A Practical Approach,* IRL Press, Washington, D.C. (1985), both herein incorporated by reference). Two sequence are said to be "complementary" to one another if they are capable of hybridizing to one another to form a stable anti-parallel double-stranded nucleic acid structure. Thus, the sequences need not exhibit precise complementarity, but need only be sufficiently complementary in sequence to be able to form a stable double-stranded structure. Thus, departures from complete complementarity are permissible, so long as such departures are not sufficient to completely preclude hybridization to form a double-stranded structure. Hybridization of a primer to a complementary strand of nucleic acid is a prerequisite for its template-dependent polymerization with polymerases. Factors (see Maniatis, T., et al., *Molecular Cloninag A Laboratory Manual,* Cold Spring Harbor Laboratories, Cold Spring Harbor, N.Y. (1982), and Haymes, B. D., et al., *Nucleic Acid Hybridization. A Practical Approach,* IRL Press, Washington, DC (1985)) which affect the base pairing of primers to their complementary nucleic acids subsequently affect priming efficiency (i.e. the relative rate of the initiation of priming by the primer). The nucleotide composition of a primer can affect the temperature at which annealing is optimal and therefore can affect its priming efficiency.

The methods of the present invention permit one to adjust the hybridization efficiency of the primers used to amplify a nucleic acid molecule. Such adjustment may either increase or decrease the difference between the respective hybridization efficiencies of two primers. The methods of the present invention thus permit one to equalize the respective hybridization efficiencies of the two primers. Several factors must be considered in order to determine the efficiency of hybridization between a primer and a target molecule. At the simplest level, the efficiency is determined by the length of the primer, the concentration of the primer, the temperature and the ionic strength of the reaction. It is also influenced by the sequence complexity of the primer, and specifically, by the number of hydrogen bonds which will form between the primer and the template. As stated above, the base pairing of an A to a T will form two hydrogen bonds; the base pairing of a G to a C will form three hydrogen bonds. Thus, at a first approximation, it is possible to more closely hybridize two different primers to two regions of a target molecule by adjusting the length and sequence complexity of the primers so that they contain the same number of hydrogen bonds. Unfortunately, additional factors, such as secondary structure, stacking energy, cooperativity in binding, etc., complicate the analysis. Thus, a determination of the conditions needed to ensure that two primers hybridize with equal efficiency requires a multi-factor analysis. Methods for determining relative primer efficiency are disclosed by Breslauer, K. J. et al. (*Proc. Natl. Acad. Sci.* (*U.S.A.*) 83:3746–3750 (1986)), Freier, S. M. et al. (*Proc. Natl. Acad. Sci.* (*U.S.A.*) 83:9373–9377 (1986)), Rychlik, W. et al. (*Nucl. Acids Res.* 17:8543–8551 (1989)), Lathe, R. (*J. Molec. Biol.* 183:1–12 (1986)), Sambrook, J. et al. (*Molecular Cloning (A Laboratory Manual)*, Cold Spring Harbor Laboratory, Cold Spring Harbor, N.Y. (1989), vol. 2, pp. 11–18), Schildkraut, C. et al. (*Biopolymers* 3:195–208 (1965)), Baldino, F. et al. (*Meth. Enzymol.* 168:761–777 (1989)), and in the Handbook of Biochemistry and Molecular Biology (Fasman, G. D., Ed.), Third Edition (1975), Nucleic Acids, Vol. 1, pp. 589, CRC Press, Cleveland, Ohio; all of which references are herein incorporated by reference. Most preferably, a determination of relative primer efficiency is performed using a computer program, such as "Oligo™ Primer Analysis Software (National Biosciences, Inc., Hamel, Minn.).

The improvement provided by the present invention results from using "pre-determined" nucleotides having altered base pairing characteristics in at least one of the primer molecules to equalize the efficiency of hybridization between (1) that primer molecule and its complement sequence on the target molecule, and (2) a second primer molecule and its complement sequence on the target molecule. The primers of the present invention are preferably 15–50 residues in length, although shorter or longer primer sequences can be employed.

DNA typically contains a polynucleotide composed of the 4 "natural" bases: A (adenine), T (thymine), C (cytosine), and G (guanine). The hydrogen bonding (or base pairing) among these nucleotides creates the double-stranded structure of a DNA molecule. An A-containing residue base pairs to a T-containing residue through the formation of two hydrogen bonds; a G-containing residue base pairs to a C-containing residue through the formation of three hydrogen bonds.

The term "pre-determined nucleotides having altered base pairing characteristics" is intended to refer to nucleotides which have bases other than the A, T, C or G naturally found in DNA. Although the pre-determined nucleotides will be capable of hydrogen bonding with naturally occurring nucleotides (such as the A, T, C or G -containing nucleotides of the template), it will form fewer hydrogen bonds with such nucleotides than would other naturally occurring nucleotides.

A nucleotide containing deoxyinosine ("dI") is a preferred example of a such a pre-determined nucleotide containing the base, inosine. It is capable of forming two hydrogen bonds with either A, C, T, or G (Barker, R., *Organic Chemistry of Biological Molecules*, Prentice-Hall, N.J. (1971)). Thus, in a preferred embodiment, when I is used in a primer (or template) in lieu of G or, in lieu of C, the base pairing efficiency is altered.

Other examples of "pre-determined" nucleotides are those which contain hypoxanthine or xanthine (each useful, for example, in lieu of G, to form two hydrogen bonds when base pairing with C), or those which contain methylated derivatives of naturally occurring bases (for example, 7-methylguanine, etc.).

In accordance with the methods of the present invention, nucleic acid amplification, such as through two primer mediated PCR, is achieved using at least one primer containing at least one of the above-described "pre-determined" nucleotides. The position, type and number of "pre-determined" nucleotide(s) in the primer sequence containing the "pre-determined" nucleotide are selected such that the efficiency of primer extension of that primer is equivalent to the efficiency of primer extension of the second primer.

As used herein, the term "equivalent efficiency of primer extension" is intended to refer to the ability of one primer, relative to a second primer, to hybridize to a complementary sequence on a template molecule, and to serve as a substrate for template-dependent primer extension by a DNA or RNA polymerase. Primer extension is said to be "template dependent" when the sequence of the newly synthesized strand of nucleic acid is dictated by complementary base pairing. A "polymerase" is an enzyme that is capable of incorporating nucleoside triphosphates to extend a 3' hydroxyl group of a nucleic acid molecule, if that molecule has hybridized to a suitable template nucleic acid molecule. Polymerase enzymes are discussed in Watson, J. D., *In: Molecular Biology of the Gene*, 3rd Ed., W. A. Benjamin, Inc., Menlo Park, Calif. (1977), which reference is incorporated herein by reference, and similar texts. Examples of polymerases include the large "Klenow" fragment of *E. coli* DNA polymerase I; Taq polymerase (Cetus); bacteriophage T7 DNA or RNA polymerase, etc. A preferred DNA polymerase is Taq polymerase (Cetus).

When an enzymatic reaction, such as a polymerization reaction, is being conducted, it is preferable to provide the components required for such reaction in "excess" in the reaction vessel. "Excess" in reference to components of the amplification reaction refers to an amount of each component such that the ability to achieve the desired amplification is not substantially limited by the concentration of that component.

Conditions or agents which increase the rate or the extent of priming, primer elongation, or strand displacement, may increase the extent of the amplification obtained with the methods of the present invention. For instance, the addition of helicases or single-stranded nucleic acid binding proteins may increase the strand displacement rate of a DNA polymerase, or may allow the use of a DNA polymerase that might not ordinarily give substantial amplification.

It is desirable to provide to the assay mixture an amount of required cofactors such as $Mg^{++}$, and DATP, dCTP, dGTP, dTTP, ATP, CTP, GTP, UTP or and the "pre-determined" nucleoside triphosphates in sufficient quantity to support the degree of amplification desired.

Extension of the primer in, for example, a cDNA-containing reaction, may be done with the same reverse transcriptase used to make cDNA. Alternatively, one can add a new DNA polymerase for cDNA extension. Removal of the RNA from the cDNA is preferably done by an RNase H treatment, or by the action of a helicase, but can be done by physical denaturation, e.g. heat, formamide, or alkali (high pH). In the latter case, if kinetics of renaturation are sufficiently high, this step must be followed by physical separation of the cDNA and RNA or by degradation of the RNA, e.g. by RNase or alkali. Note that sufficiently harsh alkali treatment may deaminate dC to form dU, causing a mutation.

Reverse transcription can be done with a reverse transcriptase that has RNase H activity. If one uses an enzyme having RNase H activity, it may be possible to omit a separate RNase H digestion step, by carefully choosing the reaction conditions.

All of the enzymes used in this amplification reaction may be active under the same reaction conditions. Indeed, buffers exist in which all enzymes are near their optimal reaction conditions. Therefore, the amplification process of the present invention can be done in a single reaction volume without any change of conditions such as addition of reactants or temperature cycling. Thus, though this process has several steps at a molecular level, operationally it may have a single step. Once the reactants are mixed together, one need not add anything or change conditions, e.g. temperature, until the amplification reaction has exhausted one or more components. During this time, the nucleic acid sequence being amplified will have been increased manyfold. The level of increase will be sufficient for many purposes; however, for some purposes the reaction may have to be repeated with fresh components to achieve the desired level of amplification.

As discussed above, the degree of amplification obtained through the use of PCR is limited if the two primers do not have equivalent efficiency of primer extension. Such a situation is frequently encountered, especially in amplification protocols such as RACE, anchored PCR, one-sided PCR, etc. (Frohman, M. A. et al., *Proc. Natl. Acad. Sci. (U.S.A.)* 85:8998–9002 (1988); Ohara, O. et al., *Proc. Natl. Acad. Sci. (U.S.A.)* 86:5673–5677 (1989), both of which references are herein incorporated by reference). In brief, these procedures facilitate the recovery of full-length cDNAs from rare transcripts. The RACE procedure results in the amplification of sequences 3' and 5' of a particular sequence known to be present in a desired molecule.

Figure 1B:
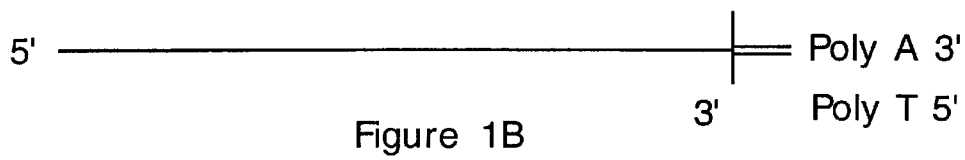
Figure 1C:
Figure 1D:
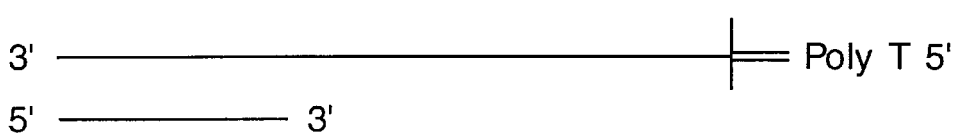
Figure 1E:
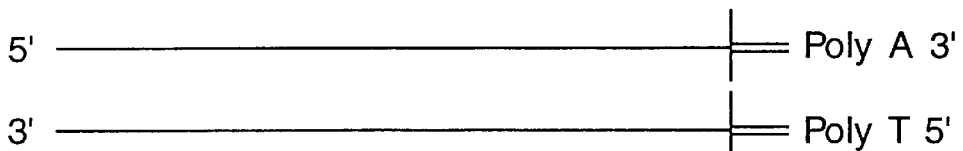

For example in the amplification of mRNA or cDNA molecule having a 3' poly-A region, two primers are typically employed. The first primer contains poly-T, and the second primer contains a sequence complementary to an internal gene sequence of the mRNA or cDNA molecule. This procedure is referred to as a 3' RACE (FIG. 1). As shown in FIG. 1A, hybridization with the first primer 3' poly T 5' is capable of hybridizing to the poly-A sequence (FIG. 1B). After primer extension and strand separation, the structure shown in FIG. 1C is obtained. After Hybridization with the first primer and with a second primer capable of hybridizing to a known sequence, the structure shown in FIG. 1D is obtained. Primer extension of both primers yields the structure shown in FIG. 1E.

Figure 2A:
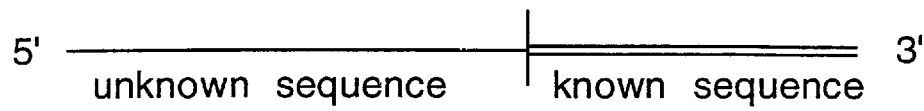
FIGS. 2A–E shows a depiction of the 5' RACE reaction.
Figure 2B:
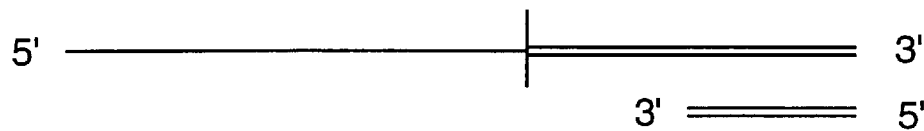
Figure 2C:
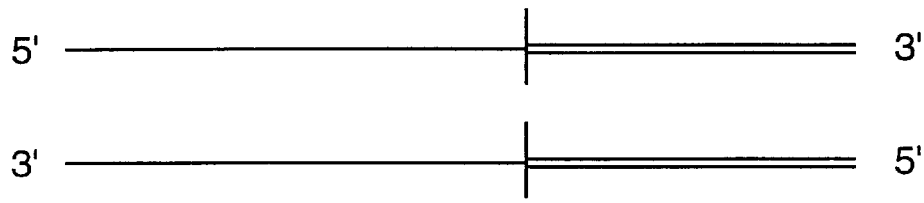
Figure 2D:
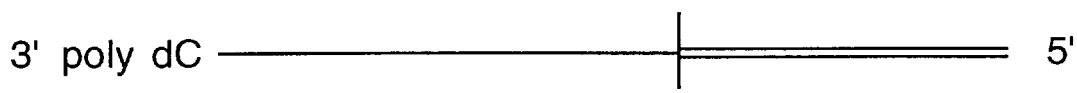
Figure 2E:
Figure 2E:
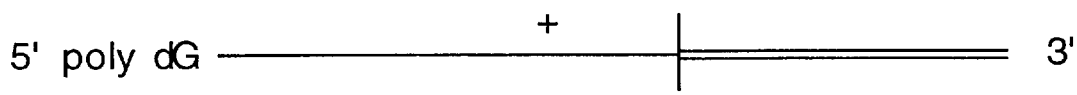
Figure 2E:
Figure 2E:
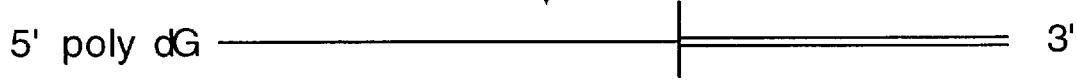
Figure 2E:
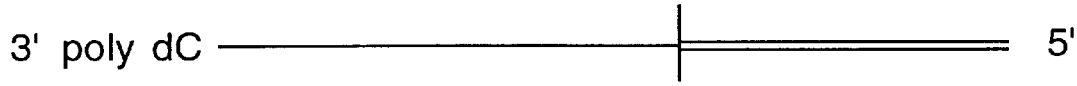
Figure 3A:
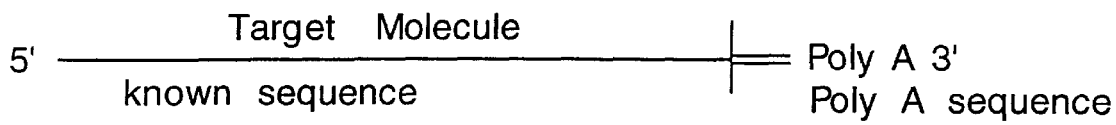
FIGS. 3A–E shows the use of inosine in the 3' RACE reaction.
Figure 3B:
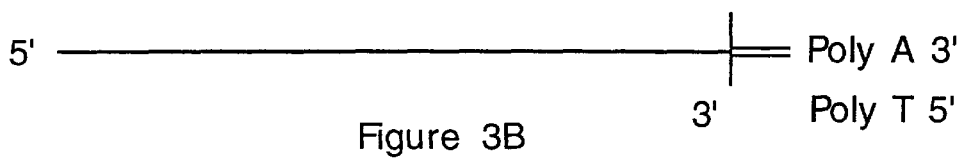
Figure 3C:
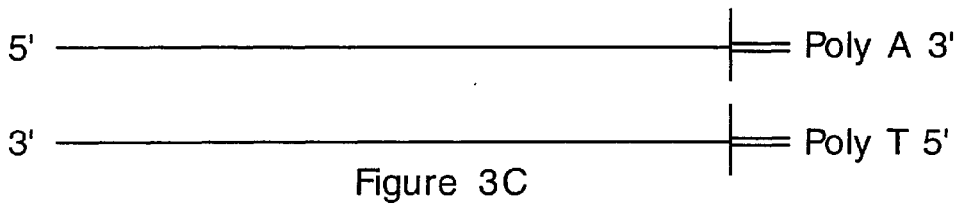
Figure 3D:
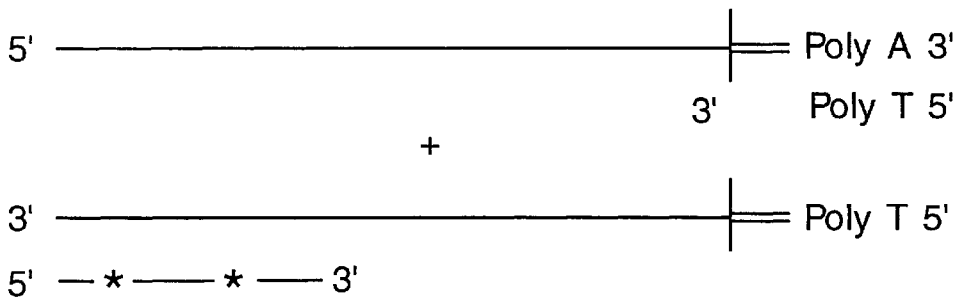
Figure 3E:
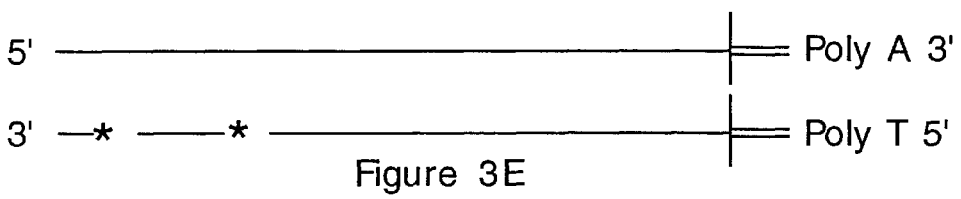
Figure 4A:
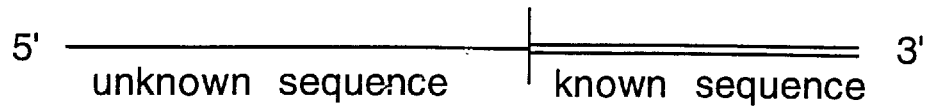
Figure 4B:
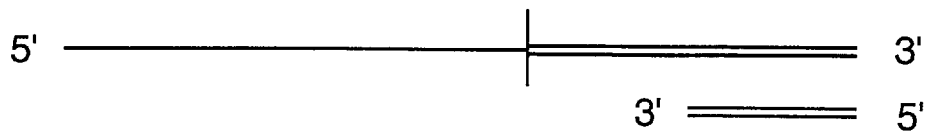
Figure 4C:
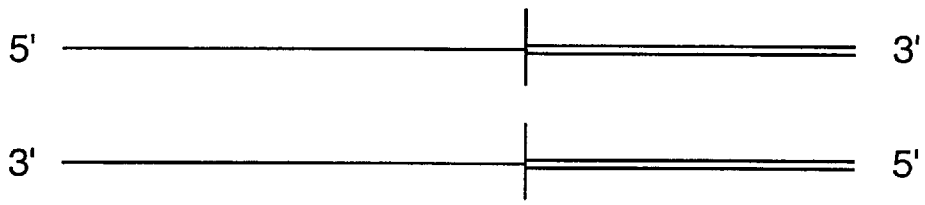
Figure 4D:
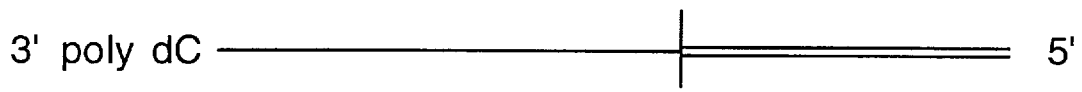
Figure 4E:
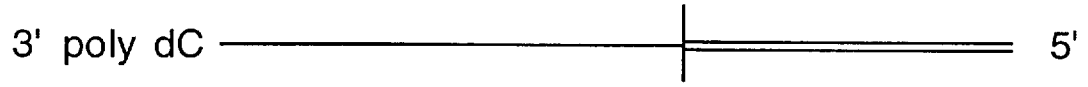

Similarly, it is often desirable to amplify a target molecule for which only one sequence specific primer is available. This can be accomplished by adding a nucleotide sequence to one end of the target molecule, or complementary copy thereof, and then using a primer which is complementary to the added nucleotide sequence (FIG. 2). The target molecule (FIG. 2A) is hybridized with a first primer capable of hybridizing to a known sequence (FIG. 2B). After primer extension, and strand separation or RNAse H degradation of target template the structure shown in FIG. 2C is obtained. This structure is treated with terminal deoxynucleotidyl transferase and dC to add a poly-dC tail to the extension product, and the other strand is of no further interest, or has been destroyed by the RNAse H treatment (FIG. 2D). The poly-dC tailed product is amplified by PCR using a poly-dG primer, and a primer capable of hybridizing to the region of known sequence (FIG. 2E). In practice, any nucleotide (A, C, T, or G) could have been used to produce the homopolymer tail and be amplified using a complementary oligonucleotide primer.

In either of the above examples, the two primers will not have the same efficiency of primer extension. In the first example, the primer having a poly-T sequence will have a lower Tm than the second primer. In the second example, the poly-dG primer will have a higher Tm than the other primer.

It should be noted that RACE procedures may generate artifact products unless nested PCR is done. Nested PCR is disclosed in U.S. Pat. Nos. 4,683,195 and 4,683,202, herein incorporated by reference. Nested PCR may also be used to eliminate non-specific amplification products. Note that nested PCR often refers to PCR with primers "nested" at both ends of the sequence, i.e. PCR conducted using 4 oligonucleotides.

As will be recognized, in both of the preceding examples a homopolymer primer (i.e. poly-T or poly-dg) is used in conjunction with a second primer having a greater sequence complexity. The present invention permits one to make the annealing efficiencies of the two primers equivalent by replacing some or all of those natural residues of the primers which form 3 hydrogen bonds with pre-determined residues capable of forming only 2 hydrogen bonds. The number, type and position of the pre-determined substitute residues is determined (as described above) such that the two primers used in the amplification have equivalent annealing efficiency.

The primer molecules themselves can be extended by the terminal deoxynucleotidyl transferase. This is generally an undesired reaction, since it leads to the formation of "primer-dimers" and decreases the efficiency of target molecule amplification. Thus, it is generally preferable to remove any primer molecules from the reaction prior to the polynucleotide kinase extension step. Once the step has been completed, the primers may be returned to the reaction. It is thereafter unnecessary to remove the primers after subsequent steps of the amplification.

The use of such replacement residues in the amplification of a polyadenylated cDNA or mRNA is illustrated in FIG. 3. The figure is identical to FIG. 1 except for the presence of inosine (represented as a "*") in the primer and extension product.

The use of the "pre-determined" nucleotides in the second primer lowers the Tm of that primer, thus permitting it to be equivalent to the Tm of the poly-T primer.

The use of "pre-determined" replacement residues in the amplification of a non-polyadenylated cDNA or mRNA sequence is illustrated below (with the designation "GG*GG*G" referring to a primer having at least one "pre-determined" nucleotide such as deoxyinosine) FIG. 4). The figure is identical to FIG. 2 except for the presence of inosine (represented as a "*") in the primer and extension product.

The use of the "pre-determined" nucleotides in the second primer lowers the Tm of that primer, thus permitting it to be equivalent to the Tm of the first primer. Note that all of the amplified sequences between the two primer sequences will be the initially present, desired sequence.

The present invention is also applicable to amplification procedures other than PCR (such as, for example, "Ligation Chain Reaction" ("LCR") described by, for example, Wu, D. Y. et al., *Genomics* 4:560 (1989), or the methods of Miller, H. I. (WO 89/06700), Davey, C. et al. (EP 329,822), Kwoh, D. (Proc. Natl. Acad. Sci. (USA) 86:1173 (1989)), etc.). Other suitable methods for amplifying nucleic acid based on ligation of two oligonucleotides after annealing to complementary nucleic acids are known in the art.

The method of this invention can be used to adjust (for example, to equalize) the annealing of the oligonucleotides prior to ligation. The ligase based methods have been used for discrimination of target molecules which are different by a single nucleotide. The methods of the present invention are also applicable for adjusting or equalizing the annealing of oligonucleotides.

The present invention thus provides a method for adjusting the hybridization efficiency of an oligonucleotide (preferably a primer) of predetermined sequence complementary to a target nucleic acid molecule (most preferably a cDNA molecule), which comprises: A) employing as the oligonucleotide an oligonucleotide wherein at least one residue is a deoxyinosine residue; and B) permitting the oligonucleotide to hybridize with the target molecule. In this method, the presence of the deoxyinosine residue effects the adjustment of the hybridization efficiency. As will be appreciated, this adjustment can either increase or decrease the hybridization efficiency of the respective molecules.

In the above-described ligation chain reaction (LCR) method, a mutation in a target molecule can be detected by using two oligonucleotides each capable of hybridizing to adjacent positions on the target molecule, such that the positions flank the site of potential mutation. The sequences of the oligonucleotides is such that if the mutation is present, the hybridized molecules will be able to anneal to one another. As will be appreciated, it is readily possible to employ oligonucleotide sequences such that the hybridized molecules will be able to anneal to one another if the mutation is not present. Thus, the capacity of the oligonucleotides to ligate to one another is "probative" of the presence of the mutation.

The present invention permits one to adjust the relative hybridization efficiency of the two oligonucleotides, by incorporating deoxyinosine into one or both oligonucleotides. It is preferable to adjust this relative efficiency to equalize the respective efficiencies of the two oligonucleotides. Such equalization can compensate for operational constraints caused by differences in the respective G-C content, size, concentration, etc. between the two oligonucleotides.

In a preferred embodiment, the ligation of the oligonucleotides results in the formation of a primer molecule that can be enzymatically extended to form a complement of the target molecule. Such amplification may be by or include PCR, but will most preferably be mediated by an isothermal extension of the primer to produce the complement to the target molecule.

The present invention may be combined with many other processes in the arts of molecular biology to achieve a specific end. Of particular interest is purifying the target sequence from the other sequences in the sample. This can be accomplished most advantageously by annealing the nucleic acid sample to an oligonucleotide that is complementary to the target and is immobilized on a solid support. A convenient support would be a micro-bead, especially a magnetic micro-bead. After being so bound, the non-target sequences could be washed away, resulting in a complete or a partial purification.

After an amplification is performed, one may wish to detect any amplification products produced. Any number of techniques known to the art may be adapted to this end without undue experimentation. Particularly advantageous in some situations is the capture of amplification products by an oligonucleotide complementary to a sequence determined by the target sequence, the oligonucleotide being bound to a solid support such as a magnetic micro-bead. Preferably, this oligonucleotide's sequence does not overlap with that of any oligonucleotide used to purify the target before the amplification. RNA:DNA hybrids formed may then be detected by antibodies that bind RNA:DNA heteroduplexes. Detection of the binding of such antibodies can be done by a number of methods well known to the art.

Alternatively, amplified nucleic acid can be detected by gel electrophoresis, hybridization, or a combination of the two, as is well understood in the art. Those in the art will find that the present invention can be adapted to incorporate many detection schemes.

Sequences amplified according to the methods of the invention may be purified (for example, by gel electrophoresis, by column chromatography, by affinity chromatography, by hybridization, etc.) and the fractions containing the purified products may be subjected to further amplification in accordance with the methods of the invention.

The present invention includes articles of manufacture, such as "kits." Such kits will, typically, be specially adapted to contain in close compartmentalization a first container which contains a pre-determined nucleotide or a primer containing a predetermined nucleotide (such as dI); a second container which contains an enzyme capable of adding a nucleotide (capable of base pairing with the pre-determined nucleotide) to a target nucleic acid molecule. The kit may additionally contain buffers, polymerase or other enzymes, instructional brochures, and the like.

Having now generally described the invention, the same will be more readily understood through reference to the following examples which are provided by way of illustration, and are not intended to be limiting of the present invention, unless specified.

EXAMPLE 1

Methods describing the application of the polymerase chain reaction to the amplification of cDNA-ends derived from low copy number mRNAs using a single gene specific primer have been described. Reported as "5'-RACE" (Frohman, M. A. et al., Proc. Natl. Acad. Sci. (U.S.A.) 85:8998 (1988)), "anchor PCR" (Loh, E. Y., et al., Science 243:217 (1989)), and "one-sided PCR" (Ohara, O. et al., Proc. Natl. Acad. Sci. (U.S.A.) 86:5673 (1989)), these methods, which facilitate the capture of sequence from $5^1$-ends of mRNA proceed through the following steps: (1) conversion of specific cDNA using a gene-specific oligonucleotide primer (GSP1); (2) homopolymeric tailing of cDNA with terminal deoxynucleotidyl transferase (TdT); and (3) PCR amplification of tailed cDNA using an "anchor primer" specific for the homopolymer tail, and a second "nested" gene-specific oligonucleotide ("GSP2") which primes upstream of the original primer used for cDNA synthesis.

The efficacy of deoxyinosine-containing oligonucleotides to prime dc-tailed cDNA in 5'-RACE procedures was tested using a model system employing an in vitro transcribed RNA analyte added to total RNA isolated from HeLa cells. The enhanced ability of a deoxyinosine-containing anchor primer to carry out specific PCR amplification of 5'-ends of low copy mRNA from complex mixtures was demonstrated in this system by direct comparison to amplification with an oligo-dG anchor primer.

MATERIALS AND METHODS

General items. SUPERSCRIPT™ RNase H⁻ reverse transcriptase (RT), *E. coli* RNase H and TdT were from Life Technologies, Inc. Taq DNA polymerase was purchased from Perkin-Elmer Cetus. Buffer components and general reagents were from either GIBCO BRL or Sigma. Deoxyribonucleoside triphosphates and ribonucleoside triphosphates were purchased as 100 mM solutions from Pharmacia.

Oligonucleotides. Oligonucleotides were synthesized by phosphoramidite chemistry using an Applied Biosystems model 380A synthesizer. Oligonucleotides greater than 35 bases were purified by denaturing polyacrylamide gel electrophoresis and were eluted from the gel matrix essentially as described by Smith, H. O. (*Methods Enzymol.* 65:371 (1980)). Other oligonucleotides were used as machine grade preparations after removal of salts and organics by PD-10 chromatography. Molar extinction coefficients and $T_m$ calculations for each oligonucleotide were calculated using the OLIGO computer program from National Biosciences (Rychlik, W. and Rhodes, R. E., *Nucleic Acids Res.* 17:8543 (1989)). For the GSP1 primer, a 24-mer oligonucleotide was employed. The GSP2 primer was 21 nucleotides long. Two anchor primers (a "G-Anchor Primer" and a GI-Anchor Primer") were employed. Both molecules had an identical 18 residue long sequence that was complementary to the target, and located immediately 5' to a poly-G sequence of 15 residues ("G-Anchor Primer") or a poly-GI sequence of 16 residues ("$^G$I-Anchor Primer"). The poly-G and poly-GI sequences differed in that nucleotides 4, 5, 9, 10, 14 and 15 of the poly-GI sequence of the GI-Anchor Primer were dI, whereas in the G-Anchor Primer, all of the nucleotides of the poly-G sequence were dG.

Preparation of RNA Analyte. RNA analyte for 5'-RACE was an in vitro transcription product from the gene for chloramphenicol acetyl transferase (CAT) (Horinouchi, S. and Weisblum, B., *J. Bacteriol.* 150:815 (1982)). In vitro transcription was performed using T7 RNA polymerase (GIBCO BRL) according to the manufacturer's recommendations. DNA template was degraded using RNase-free DNase (GIBCO BRL). RNA was extracted once using a 50:50 mixture of phenol:chloroform and purified by Sephadex G-50 (Pharmacia) chromatography. CAT RNA was diluted in DEPC treated water, and stored at −70° C.

Preparation of Total HeLa RNA. Total RNA was isolated from HeLa cells by guanidinium thiocyanate extraction and equilibrium centrifugation in CsTFA essentially as described by Okayama, H. et al. (*Methods Enzymol.* 154:3 (1987)) using an RNA Extraction Kit from Pharmacia. 5'-RACE. Varying amounts of in vitro transcribed CAT RNA were combined with 1 µg of total RNA from HeLa cells, 1 pmole of oligo GSP1, and DEPC treated water in a final volume of 14 µl. Mixtures were heated at 70° C. for 10 min to denature secondary structure, and then chilled on ice. Following a brief centrifugation, the remainder of the first strand synthesis components was added. Reactions were equilibrated to 42° C. for 2 min prior to the addition of SUPERSCRIPT RT. First strand syntheses were performed in final volumes of 20 µl consisting of 20 mM Tris-HCl (pH 8.4), 50 mM KCl, 2.5 mM MgCl$_2$, 100 µg/ml BSA, 10 mM DTT, 1 pmole GSP1, RNA and 200 units SUPERSCRIPT RT and were incubated 30 min at 42° C. Following first strand conversion, reactions were equilibrated to 55° C. and 2 units *E. coli* RNase H was added to destroy CAT RNA template. Specific cDNA products were purified, tailed with dCTP, and amplified by PCR as described below.

Primer and unincorporated dNTPs were separated from cDNA using a 30K low-binding Ultrafee-MC filter unit from Millipore essentially according to the manufacturer's recommendations. Four successive wash steps with 350 µl 0.1X TE buffer were used to insure sufficient removal of first stand primer. Centrifugations were at 2,000 x g for 5 min. Purified cDNA was recovered with a final rinse of 50 µl sterile H$_2$O, transferred to a 0.5 ml micro-tube, lyophilized till dry using a Savant Speed-Vac, then dissolved in 19 µl 10 mM Tris-HCl (pH 8.4), 25 mM KC., 1.25 mM MgCl$_2$, 50 µg/ml BSA, and 200 µM dCTP. The mixture was denatured 2 min, 94° C., then chilled on ice, and the contents collected by brief centrifugation. Homopolymeric tailing was initiated by addition of 10 units TdT and incubated 5 min, 37° C, then 10 min, 65° C.

Tailed cDNA was amplified directly from TdT reactions without prior dilution. Following a brief centrifugation to collect tailed cDNA, one-tenth of each tailing reaction, 2 µl aliquots, from were amplified by PCR. Amplification reactions were performed in 50 µl volumes composed of 20 mM Tris-HCl (pH 8.4), 50 mM KCl, 2.5 mM MgCl$_2$, 100 µg/ml BSA], 0.2 mM each dNTP, 4 pmoles GSP2, 4 pmoles Anchor Primer (either the GI-Anchor Primer or the G-Anchor Primer), tailed cDNA and 1 unit Taq DNA polymerase (Perkin Elmer-Cetus). Reactions were assembled on ice, overlaid with 50 µl light mineral oil (Sigma), and placed into a DNA Thermalcycler (Perkin Elmer Cetus) which had been equilibrated to 94° C. Following an initial 5 min denaturation at 94° C., PCRs were temperature cycled through 30 cycles as follows: 45 s at 94° C. (denaturation); 25 s at 55° C. (annealing); and 3 min at 72° C. (extension). After the final cycle an additional 7 min extension at 72° C. was performed and then reactions were held at 4° C.

Control reactions omitted either RNA analyte, reverse transcriptase, or TdT. A quantified dc-tailed cDNA target, derived from the CAT RNA analyte, was used as a positive control.

Analysis of Amplification Products. Following amplification one-fifth, 10 µl, of each PCR was analyzed by electrophoresis on a 1.5% agarose/TBE gel. Amplified DNA was visualized by ethidium bromide staining and photographed.

RESULTS

Based on sequence analysis of the CAT RNA analyte, primers used for amplification were predicted to produce a 930 bp product from dc-tailed CAT cDNA target. This product was observed in PCRs primed with GSP2 and either the GI-anchor primer or the G-anchor primer. However, sensitivity and band intensity was approximately 10 fold greater in PCRs containing equivalent amounts of target which were amplified using the GI-anchor primer as compared to amplifications which used the G-anchor primer. The 930 bp product was clearly visible in 5'-RACE reactions initiated with as few as $10^5$ copies of RNA analyte when the GI-anchor primer was used for amplification. However, product was not visible in a parallel reaction amplified with the G-anchor primer. Band intensity of the 930 bp product resulting from 5'-RACE reactions containing $10^6$ copies of CAT RNA analyte was approximately 10 fold greater in PCRs performed with the GI-anchor primer as compared to PCRs primed with the G-anchor primer.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. An improved method for amplifying the concentration of a target nucleic acid molecule by using a first and a second primer to form a double-stranded nucleic acid molecule, wherein said first primer hybridizes to a first strand of said double-stranded nucleic acid molecule, and said second primer hybridizes to a second strand of said double-stranded nucleic acid molecule, and wherein said primers exhibit different $T_m$s with respect to one another, when hybridized to said-double stranded nucleic acid molecule, said improved method comprises the steps:

(a) replacing at least one residue in at least one of said primers with at least one nucleotide having altered base pairing characteristics, wherein said replacement equalizes the $T_m$s of the first and second primers with respect to one another, when hybridized to said double-stranded nucleic acid molecule;

(b) performing the template-dependent extension of said first primer, said first primer being hybridized to a first strand of said double-stranded molecule, wherein said extension forms a second strand of nucleic acid complementary to said first strand of said double-stranded nucleic acid molecule;

(c) performing the template-dependent extension of said second primer, by extending said second primer, said second primer being hybridized to said second strand of said double-stranded nucleic acid molecule, wherein said extension forms a copy of said first strand of said double-stranded nucleic acid molecule;

(d) performing the template-dependent extension of said copy of said first stand, to thereby form a copy of said second strand of said double-stranded nucleic acid molecule; and (e) repeating steps (b), (c) and (d) to thereby achieve said amplification of said target nucleic acid molecule.

2. The method according to claim 1, wherein said nucleotide having altered base pairing characteristics is selected from the group consisting of hypoxanthine, xanthine and a methylated derivative of a naturally occurring base.

3. The method of claim 1, wherein said nucleic acid molecule is an RNA molecule.

4. The method of claim 3, wherein said RNA molecule is single-stranded.

5. The method of claim 3, wherein said RNA molecule is double-stranded.

6. The method of claim 1, wherein said nucleic acid molecule is a DNA molecule.

7. The method of claim 6, wherein said DNA molecule is single-stranded.

8. The method of claim 6, wherein said DNA molecule is double-stranded.

9. The method of claim 1, wherein both of said primers contain at least one nucleotide having altered base pairing characteristics.

10. The method of claim 1, wherein said nucleic acid molecule being amplified is polyadenylated at its 3' end, and wherein one of said primers contains a poly-T sequence, and the other of said primers contains at least one nucleotide having altered base pairing characteristics.

11. The method of claim 1, wherein said nucleic acid molecule being amplified, copy thereof or complementary copy thereof, has been extended to contain a 3' sequence, and wherein one of said primers is capable of hybridizing to said 3' sequence, said primer containing at least one nucleotide having altered base pairing characteristics.

12. The method of claim 1, wherein at least one of said primers is extended using a thermostable DNA polymerase.

13. The method of claim 12, wherein said thermostable DNA polymerase is Taq polymerase.

14. An improved method for amplifying the concentration of a target nucleic acid molecule by using a first and a second oligonucleotide primer, wherein said first and second primers hybridize to a nucleic acid molecule, such that they may be ligated to one another and thereby form said target molecule, and exhibit different $T_m$s with respect to one another, when hybridized to said nucleic acid molecule, said improved method comprising the steps:

(a) replacing at least one residue in at least one of said primers with at least one nucleotide having altered base pairing characteristics, wherein said replacement equalizes the $T_m$s of the first and second primers with respect to one another, when hybridized to said nucleic acid molecule;

(b) hybridizing said first and second primers to said nucleic acid molecule; and (c) ligating said hybridized first and second primers to one another, wherein said ligation forms said target molecule.

15. The method of claim 14, wherein said target nucleic acid molecule is a cDNA molecule.

16. The method of claim 14, wherein said oligonucleotides when ligated together form a primer, and wherein said primer is isothermally extended to produce a complement to the target molecule.

17. The method of claim 14, wherein the capacity of said oligonucleotides to ligate to one another is probative of the presence of a mutation.

* * * * *